United States Patent [19]  [11] 4,046,782
Kollar  [45] Sept. 6, 1977

[54] PROCESS FOR THE INDUSTRIAL PRODUCTION OF ETHYLENE OXIDE AND AROMATIC ACID

[76] Inventor: John Kollar, 6 Spencer Court, Wyckoff, N.J. 07481

[21] Appl. No.: 575,643

[22] Filed: May 8, 1975

[51] Int. Cl.$^2$ ............................................. C07D 301/06
[52] U.S. Cl. .......................... 260/348.32; 260/524 R; 260/599; 260/618 C
[58] Field of Search ................................ 260/348.5 V

[56] References Cited

FOREIGN PATENT DOCUMENTS 1,506,303  11/1967  France
1,080,462  8/1967  United Kingdom ......... 260/348.5 V Primary Examiner—Norma S. Milestone
Attorney, Agent, or Firm—H. Hume Mathews

[57] ABSTRACT

A process for the industrial production of ethylene oxide and an aromatic acid by reacting oxygen with ethylene and a methyl aromatic compound in the liquid phase. Oxygen and ethylene are passed into a liquid mono or poly methyl aromatic compound and reacted therein to produce ethylene oxide and methyl aromatic oxidates. The aromatic oxidates are then further oxidized to produce aromatic acids. When the methyl aromatic compound used is toluene the acid produced is benzoic acid, from p-xylene, terephthalic acid is produced; from m-xylene isophthalic acid is produced; and from pseudocumene (1, 2, 4 trimethyl benzene) trimellitic acid is produced.

30 Claims, 1 Drawing Figure

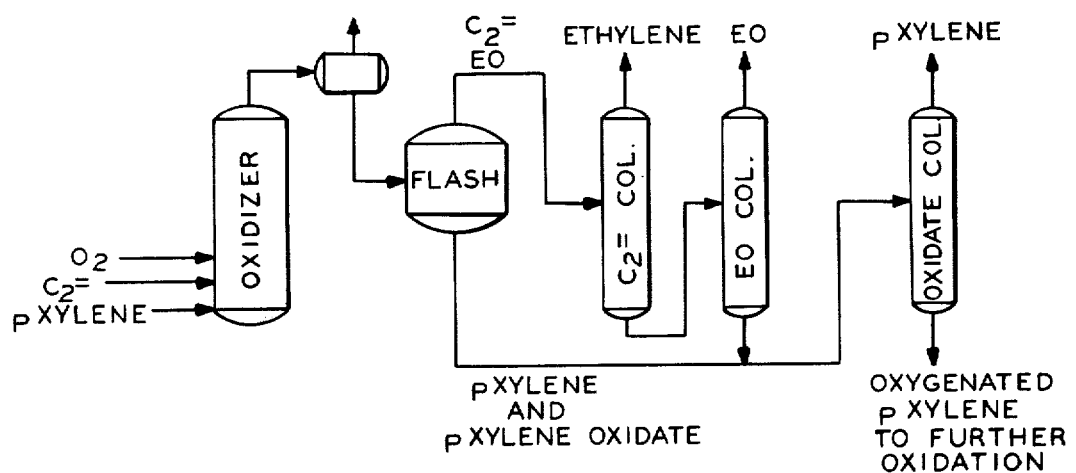
SIMPLIFIED FLOWSHEET

PROCESS FOR THE INDUSTRIAL PRODUCTION OF ETHYLENE OXIDE AND AROMATIC ACID

FIELD OF THE INVENTION

Because of the great industrial importance of ethylene oxide a vast research effort has been directed toward its efficient production. Despite these efforts no new efficient processes have been reported and the standard of the industry remains the vapor phase oxidation of ethylene over a silver catalyst as illustrated in U.S. Pat. NO. 3,693,474 wherein ethylene oxide is produced in a 65-70 M% selectivity. About ⅓ of the ethylene is effectively burned to carbon dioxide and water.

Industrially important advances in the art have been made in the epoxidation of propylene to propylene oxide. As illustrated in U.S. Pat. No. 3,351,635, propylene is efficiently epoxided to propylene oxide by reaction with organic hydroperoxides in the presence of catalysts.

Propylene oxide has also been produced by co-oxidizing propylene with acetaldehyde to produce propylene oxide and acetic acid by affecting the oxidation in the presence of a nitrile such as acetontrile as shown by Union Carbide in German Pat. No. 2,061,522, and by the catalytic oxidation of propylene and the catalytic co-oxidation of propylene and various aromatic solvents in French Pat. No. 1,506,303.

In British patent specification No. 1,080,462, co-oxidation of olefins with organic compounds that readily form peroxy compounds is taught. Modest results are obtained when acetaldehyde and propylene are co-oxidized (i.e. about 50 M of epoxide are produced for 100 M of acetaldehyde reacted). With hydroperoxide formers such as ethyl benzene and cumene about 25 M of epoxide are formed for every 100 moles of hydrocarbon oxidized. When the readily oxidized acetaldehyde is co-oxidized with ethylene only 13 M of ethylene oxide are formed per 100 M of acetaldehyde reacted according to the corresponding journal article from Dokl. Akad Nauk. S.S.R. 167 (3) 579-82 (1966) Russ.

Despite the advent of new techniques for the more efficient industrial production of propylene oxide an efficient method for the corresponding industrial production of ethylene oxide has not heretofore been shown. The reason for this may lie in the relative unreactivity of ethylene. For example, D. Swern shows in JACS 69, 1962 (1947) that relative reactivities of olefins toward epoxidation vary greatly depending upon the size and structure of the olefin. Typically the following is a generalized relative reactivity of olefins.

| Relative Rates of Reactivity | |
|---|---|
| $CH_2 = CH_2$ | 1 |
| $RCH = CH_2$ | 24 |
| $RCH = CHR$ | 500 |
| $R_2C = CHR$ | 6500 |

Despite the relative unreactivity of ethylene to epoxidation, it has been found according to the present invention that ethylene oxide can be produced very selectively at high reaction rates by co-oxidizing ethylene with methyl aromatics. With this invention it is possible to achieve significantly greater than 100 M of epoxides per 100 moles of methyl groups oxidized if practiced according to one embodiment of this invention. Further according to the invention aromatic oxidates are produced which can readily be converted to the industrially important aromatic acids such as terephthalic acid, isophthalic acid, benzoic acid and trimellitic acid.

Terephthalic acid is currently produced by a number of different processes such as the direct oxidation of p-xylene by a bromine promoted heavy metal oxidation catalyst such as cobalt and manganese. Another process uses acetaldehyde as an activator for the cobalt catalyst to effect the oxidation. Still another uses very high levels of cobalt to maintain oxidation activity. A process which utilized methyl ethyl ketone as an activator for a cobalt catalyst was practiced commercially for a short time at one installation.

The Henkel process produces terephthalic acid via isomerization of phthalic anhydride or by the reaction of benzoic acid to terephthalic acid and benzene.

The Witten-Hercules process produced dimethyl terephthalate by oxidizing p-xylene and/or methyl toluate to toluic acid and the monomethyl ester of terephthalic acid.

The bulk of terephthalic acid and dimethyl terephthalate is used to form the polymer polyethylene terephthalate which is used as film for magnetic tape, electrical insulation, packaging and photographic applications. Its largest use, however, is in fibers.

Isophthalic acid is also currently produced by processes such as those referred to above for the production of terephthalic acid. Uses for isophthalic acid include use for the manufacture of unsaturated polyester resins, in alkyd resins for paints, use as a plasticiser, fiber modifier and as a base for a high thermal stability monomer.

Benzoic acid can be produced by the oxidation of toluene, with a number of different catalysts.

Trimellitic acid is produced from pseudocumene when oxidized in the presence of a heavy metal catalyst promoted with bromine in an acetic acid solvent.

According to the present invention these aromatic acids can be co-produced in a new industrial process for the manufacture of ethylene oxide. Particularly valuable embodiments of the present invention are those which co-produce ethylene and terephthalic acid, these being the two basic raw materials for the manufacture of polyesters (Dacron).

GENERAL DESCRIPTION OF THE INVENTION

The invention is a new process for the industrial manufacture of previously known products of great commercial importance, namely ethylene oxide and aromatic carboxylic acid or aromatic polycarboxylic acid. The process conditions are such as to provide high yields of ethylene oxide relative to the yield of co-product, in a ratio sufficient to make the process economically feasible for industrial use.

In the process of the invention oxygen is reacted with ethylene and a methyl aromatic (specifically toluene, xylene, or pseudocumene) in the liquid phase, without the necessity of a catalyst, to produce ethylene oxide and an oxidate of the said mono or poly methyl benzene in controlled relative concentrations. Ethylene oxide is removed from the reaction medium and the said mono or poly methyl benzene oxidate is converted to the corresponding benzene carboxylic acid, the final products of the invention being ethylene oxide and terephthalic acid when p-xylene is the co-oxidant, ethylene oxide and isophthalic acid when m-xylene is the co-oxidant, ethylene oxide and trimellitic acid when pseudocumene is the co-oxidant, and ethylene oxide and benzoic acid when toluene is the co-oxidant. The benzoic acid product of this process is usable directly or can be used as an intermediate for the production of terephthalic acid and benzene via the Henkel process, or alternatively can be utilized as the starting material for the production of phenol via a known oxidative decarboxylation technique. The production of other aromatic acids is also contemplated.

Preferred reactants are ethylene and p-xylene, which are reacted with oxygen in the liquid phase (i.e. the p-xylene is in the liquid phase and the ethylene and oxygen are introduced as gases into the said liquid for reaction therein and therewith) with the final products being ethylene oxide and terephthalic acid. The operation of the process, as applied to these three reactants, oxygen, p-xylene and ethylene, may be summarized as follows.

It is preferred to operate the process in such a manner that high concentrations of both ethylene oxide and aromatic oxidate are avoided, because these two products can, under the conditions of the reaction, themselves react to form various ethylene oxide adducts. One preferred method of accomplishing this result (i.e. avoiding high concentrations of both ethylene oxide and aromatic oxidate in the reaction mixture) is to operate in such a way that the desired low concentrations of ethylene oxide and aromatic oxidate are maintained by distilling away from the reaction effluent (the mixed products of the reaction) only the unreacted ethylene and the ethylene oxide while returning the unreacted, undistilled aromatic and the aromatic oxidate and the recovered ethylene back to the reaction zone to allow additional production of ethylene oxide and provide a higher concentration of aromatic oxidate in the reaction zone. In this fashion the ethylene oxide is kept from reacting to an undue extent with the aromatic oxidate and the ethylene oxide is obtained as product with the need to distill only a minimum quantity of material.

Preferably, the per pass conversion of ethylene is maintained between 5% and 60%, depending upon the reaction conditions. The reaction should be carried out at a temperature (the temperature of the liquid in the reaction zone) within the range from 150° C to 300° C, and preferably within the range from 175° C to 250° C. Reaction times are lower at the elevated temperatures, of course, and generally are from 1 min. to 5 hrs. Preferably, the reaction time should be in the range from 2 min. to 1 hr.

Pressure in the reaction zone (the pressure of the liquid in the reaction zone) should be maintained in the range from 100 p.s.i.a. to 4000 p.s.i.a., and preferably within the range from 750 p.s.i.a. to 2000 p.s.i.a.

The co-oxidation method of this invention can be carried out as a batch process, a semi-continuous or continuous process, or even a combination thereof. For commercial purposes continuous operation is preferred. The co-oxidation of any one of the methyl aromatic compounds with ethylene can be effected continuously in a number of different ways, either with or without recycling part of the oxidate components, as explained below.

One method is to react ethylene with oxygen in the presence of a mono or poly methyl aromatic compound to obtain a reaction mixture containing ethylene, ethylene oxide, methyl aromatic and a methyl aromatic oxidate having a composition rich in aldehyde and alcohol derivatives and low in acid derivatives of the methyl aromatic. No recycle of oxidate is effected; after separation by distillation the total oxidate is further oxidized to the aromatic acid. The accompanying drawing illustrates this method.

A second method of effecting the reaction is to operate the reaction with recycle of part of the aldehyde and alcohol oxidation products of the methyl aromatic with only the acid component of the oxidate exiting the co-oxidation. When the acid product is the mono acid (benzoic acid) it is purified for further use. When the ultimate acid product is poly-functional the oxidate is sent to further oxidation to produce the di- or tri-acid. This method of operation has the advantage in that it allows for the production of a greater ratio of ethylene oxide which is a desirable feature.

A third method of operation is to oxidize the methyl aromatic in the absence of ethylene to a conversion of from 2–60% to obtain an oxidation reaction mixture rich in oxygenated aromatic and to further react this mixture directly, or after concentrating it with respect to oxygenated aromatic compound by removing some or all of the methyl aromatic compound, with ethylene and oxygen to yield ethylene oxide and further oxygenated aromatic oxidate. This procedure allows for the utilization of much milder operating conditions for the practice of this invention since the concentrated oxygenated aromatic compounds are more readily reacted. However, this method of operation yields a lower ratio of the desired ethylene oxide.

REACTANTS

The amount of ethylene that can be employed in the reaction medium can be from near 0 wt.% to 20 wt.% but it is preferred to operate with from 1 wt.% to 9 wt.% ethylene dissolved in the reaction medium at reaction conditions. Use of higher ethylene concentrations can be used as another way of improving the molar ratio of ethylene oxide obtained per mole of methyl aromatic oxidized. However, operation at very high ethylene concentrations imposes, because of the high pressure required to maintain such concentrations, an economic penalty.

Any oxygen containing gas may be utilized such as air or mixtures of oxygen and other gases such as ethylene, ethane, carbon monoxide, carbon dioxide, nitrogen, etc. It is preferred to use a commercial grade of oxygen in conjunction with recycled gas from the reaction system. The partial pressure of the oxygen should be within the range from 0.1 p.s.i.a. to 500 p.s.i.a. and preferably within the range from 5 p.s.i.a. to 100 p.s.i.a.

The mono or poly methyl aromatic is employed in liquid form, preferably in combination with an inert solvent such as benzene, napthalene or biphenyl. The nature of the solvent should be such that under the reaction conditions it is essentially non-reactive and non-corrosive. The preferred solvents, for low cost and non-reactivity are mono and poly nuclear aromatics, specifically those named above, but other materials may be used.

Use of the inert solvents as described above, enables one to increase the molar ratio of ethylene oxide obtained per mole of methyl aromatic oxidized. The most preferred ratio of the inert solvent to the p-xylene (exclusive of dissolved ethylene) is $$\frac{\text{inert solvent}}{\text{p-xylene}} = \text{from 0-3}$$
(i.e. 100% of p-xylene to 25% p-xylene)

With m-xylene the preferred ratio of solvent to meta-xylene is likewise from 0–3. For the less methylated aromatic toluene, the need for solvent is less beneficial whereas with the more methylated aromatics such as pseudocumene the need for an inert solvent is greater.

ADDITIONAL REACTANTS

In cases where it is desired to obtain further reactant products of ethylene oxide, such as ethylene glycol or glycol acetates, this can be achieved directly by adding to the reaction medium, described above, either water or acetic acid or other organic acid. It then becomes possible to produce, by judicious choice of the amount of water or acid added, essentially only small amounts of diethylene glycol or glycol acetates and/or mixtures thereof as by-products.

The amount of the added water or acetic acid is not critical but should exceed the stoichiometric requirements of the produced ethylene oxide if the further derivative is desired. The amount of the excess should preferably be 4–100 moles/mole of ethylene reacted. The water formed in oxidation of the p-xylene can furnish some of this water.

THE CO-OXIDATION PRODUCTS

The direct products of the oxygen-p xylene-ethylene reaction of the preferred form of this invention as described above are the p-xylene oxidates, largely p-methyl benzyl alcohol, p-tolualdehyde, p-toluic acid (and/or derivatives of these) and ethylene oxide.

When practiced with recycle of p-tolualdehyde and p-methyl benzyl alcohol the direct products are predominantly p-toluic acid (and/or derivatives) and ethylene oxide. Analogous products are obtained when m-xylene is employed in place of the p-xylene, the oxidate being largely m-methyl benzyl alcohol, m-tolualdehyde and m-toluic acid or, with recycle, m-toluic acid.

The direct products of the oxygen-toluene-ethylene reaction of this invention are the toluene oxidates, largely benzaldehyde, benzyl alcohol and benzoic acid (and/or derivatives of these) and ethylene oxide. With recycle of the aldehyde and alcohol to the co-oxidation the predominant product is benzoic acid (and/or derivatives) and ethylene oxide.

The direct products of the oxygen-pseudocumene-ethylene reaction of this invention are the pseudocumene oxidates, largely the mono-functional aldehyde, alcohol and acid (and/or derivatives of these) and ethylene oxide.

FINAL PRODUCTS

Following removal from the reaction medium, as described above, the said p-xylene oxidates are converted to terephthalic acid by reacting the p-xylene oxidate with oxygen in an acetic acid solvent in the presence of a catalyst system consisting of cobalt, manganese and bromine at a temperature of 220° C in a fashion similar to the teaching of U.S. Pat. No. 3,092,658. Alternatively the p-xylene oxidate can be reacted in an acetic acid medium with oxygen in the presence of a cobalt catalyst with an activator such as acetaldehyde or methyl ethyl ketone as shown in British patent specification No. 1,237,298 and U.S. Pat. No. 2,853,514. Other techniques shown to effect the oxidation of p-xylene to terephthalic acid can also be employed with the p-xylene oxidate.

The oxidates from the toluene, the m-xylene system likewise can be further reacted to benzoic acid and isophthalic acid, respectively, by any of the above mentioned procedures. Pseudocumene oxidate, however, is generally reacted to trimellitic acid by only the bromine assisted heavy metal catalyst system as taught in U.S. Pat. No. 3,092,638.

Ethylene oxide is, of course, the most desired, or most valuable, final product of the invention.

In the alternative method, as described above, the final products are ethylene oxide and ethylene glycol, in addition to the aromatic acid.

The same general process conditions, as set forth above with respect to the practice of the invention utilizing p-xylene, also apply as illustrated in the specific examples hereinbelow, to the process as carried out with ortho or meta xylene or with toluene or pseudocumene. Of course, the end products are different in that in addition to ethylene oxide in all cases the other coproduct when p-xylene is used is terephthalic acid, when m-xylene is used is isophthalic acid, when toluene is used is benzoic acid, and when pseudocumene is used is trimellitic acid (i, 2, 4 benzene tricarboxylic acid).

SPECIFIC EXAMPLES OF THE INVENTION

EXAMPLE I

Into a 500 cc., 316 s.s. pressure vessel equipped with magnetic agitation is placed a liquid charge of 43 g. of p-xylene which is then pressurized with oxygen to 15 p.s.i.a., then pressurized with ethylene. The reaction mixture is heated to 205° C by immersion in a constant temperature bath and reacted for 10 min. at approximately that temperature with agitation at a system pressure of 330 p.s.i.g. At the end of the reaction time the pressure vessel is quenched in cold water to stop the reaction. The reaction mixture is withdrawn and analyzed. The liquid phase effluent is found to contain 0.44 wt.% ethylene oxide, 6.0 wt.% p-tolualdehyde, 4.9 wt.% p-methyl benzyl alcohol free and combined, and 2.1 wt.% p-toluic acid free and combined. The selectivity to ethylene oxide is greater than 95 M%.

EXAMPLE II

Example I is repeated using a greater pressure of ethylene. At reaction conditions the system pressure is 640 p.s.i.g. The reaction mixture is reacted for 10 min. at 205° C with agitation, withdrawn and analyzed. The liquid phase effluent is found to contain 1.03 wt.% ethylene oxide, 6.0 wt.% p-tolualdehyde, 4.75 wt.% p-methyl benzyl alcohol free and combined, and 1.75 wt.% p-toluic acid free and combined. The ethylene to ethylene oxide selectivity is 90+ M%.

EXAMPLE III

Example I is repeated with a charged oxygen partial pressure of 40 p.s.i.a. and an ethylene charge that is reacted at 205° C for 10 min. with agitation at a system pressure of 1500 p.s.i.g. The reaction mixture is withdrawn and analyzed. The iquid phase effluent is found to contain 1.28 wt.% ethylene oxide, 3.55 wt.% p-tolualdehyde, 2.90 wt.% p-methyl benzyl alcohol free and combined, and 0.75 wt.% p-toluic acid free and combined.

EXAMPLE IV

Example I is repeated with a charged oxygen partial pressure of 45 p.s.i.a. and an ethylene charge that is reacted at 175° C for 30 min. at a system pressure of 1410 p.s.i.g. The liquid phase is found to contain 0.65 wt.% ethylene oxide, 2.1 wt.% p-tolualdehyde, 1.85 wt.% p-methyl benzyl alcohol free and combined, and 0.45 wt.% p-toluic acid free and combined. The selectivity to ethylene oxide is about 95 M%.

EXAMPLE V

Example I is repeated with a charged oxygen partial pressure of 30 p.s.i.a. and an ethylene charge that is reacted at 190° C for 30 min. at a system pressure of 610 p.s.i.g. The liquid phase effluent is found to contain 1.25 wt.% ethylene oxide, 6.3 wt.% p-tolualdehyde, 5.0 wt.% p-methyl benzyl alcohol moieties and 2.5 wt.% p-toluic acid moieties.

EXAMPLE VI

Example V is repeated at a system pressure of 1310 p.s.i.g. The liquid phase effluent contains 1.46 wt.% ethylene oxide, 4.95 wt.% p-tolualdehyde, 3.85 wt.% p-methyl benzyl alcohol moieties and 1.1 wt.% p-toluic acid moieties.

EXAMPLE VII

Into a pressure vessel equipped with magnetic agitation is placed a charge that at the reaction temperature of 205° C is composed of about 2.9 wt.% ethylene, 55.9 wt.% p-xylene, 41.1 wt.% benzene at a partial pressure of oxygen of 60 p.s.i.a. and a system pressure of 1125 p.s.i.g. The reaction mixture is reacted for 10 min. Analysis of the liquid phase effluent shows that 1.26 wt.% ethylene oxide has been produced as well as 1.0 wt.% p-tolualdehyde, 1.5 wt.% p-methyl benzyl alcohol moieties, and 0.75 wt.% p-toluic acid moieties.

EXAMPLE VIII

Example VII is repeated with the reaction mixture being reacted for 30 min. at 190° C and a system pressure of 1050 p.s.i.g. The liquid phase effluent contains 0.96 wt.% ethylene oxide. The ethylene oxide selectivity is 95+ M%.

EXAMPLE IX

Into a pressure vessel equipped with magnetic agitation is charged 35.1 g. p-xylene and 10.0 g. $H_2O$. The vessel is pressurized with 60 p.s.i.a. oxygen and then pressurized with ethylene. The reaction vessel is heated to 205° C and reacted for 15 min. at a system pressure of 2200 p.s.i.g. After rapid quenching the contents of the reactor are discharged. Two phases are obtained. The water phase is found to contain 2.0 wt.% ethylene glycol and an undetermined amount of diethylene glycol.

EXAMPLE X

Example IX is repeated with 28.3 g. p-xylene and 10.0 g. water as the charge, with 60 p.s.i.a. oxygen and ethylene pressure such that at 175°-180° C the system pressure is 2100 p.s.i.g. After cooling two phases are obtained and analyzed. The water layer contains 2.96 wt.% ethylene glycol and 0.20 wt.% diethylene glycol. The organic phase contains 1.85 wt.% p-tolualdehyde, 1.4 wt.% p-methyl benzyl alcohol moieties and 0.4 wt.% p-toluic acid moieties.

EXAMPLES XI

Example IX is repeated with 35.0 g. p-xylene and 10.0 g. acetic acid with 60 p.s.i.a. oxygen and ethylene pressure such that at 205° C the system pressure is 1800 p.s.i.g. The reaction mixture is reacted for 30 min. After cooling two phases are obtained. In the acetic acid phase is found 3.75 wt.% ethylene glycol diacetate and 1.4 wt.% ethylene glycol monoacetate.

EXAMPLE XII

Example VII is repeated with a liquid mixture of 3.3 wt.% ethylene, 56.7 wt.% p-xylene, and 40.3 wt.% benzene reacting with oxygen at an initial partial pressure of 60 p.s.i.a. for 30 min. at 175° C. The liquid phase reaction effluent contains 0.99 wt.% ethylene oxide.

EXAMPLE XIII

Into a pressure vessel equipped with magnetic agitation is placed 200 g. of p-xylene and 0.6 g. of cobalt octanoate solution containing 5 wt.% cobalt. The reaction mixture is brought to 155° C and maintained at that temperature for 30 min. while air is passed through reaction mixture at 60 p.s.i.g. system pressure. The p-xylene oxidate is shown to contain 3.40 wt.% p-tolualdehyde, 2.2 wt.% p-methyl benzyl alcohol and 1.4 wt.% p-toluic acid.

The p-xylene oxidate from the above is used as a charge in the co-oxidation. A liquid composition containing 3.2 wt.% ethylene, and 96.8 wt.% of p-xylene oxidate is reacted with oxygen at 60 p.s.i.a. for 20 min. at 190° C. The liquid phase effluent is shown to contain 1.15 wt.% ethylene oxide, 3.25 wt.% p-tolualdehyde, 2.55 wt.% p-methyl benzyl alcohol moieties and 4.75 wt.% p-toluic acid moieties. The ethylene oxide is recoverable by distillation. The oxygenated xylene materials are obtained as a bottoms fraction when p-xylene is distilled therefrom. The oxygenated xylene derivatives are added to acetic acid and catalyst consisting of $CoBr_2$ and $MnBr_2$ and reacted with the oxygen (in air) at 220° C for 30 min. at a system pressure of 300 p.s.i.g. to produce terephthalic acid.

EXAMPLE XIV

Into a pressure vessel equipped with magnetic agitation is placed a liquid charge of 3.5 wt.% ethylene, 63.7 wt.% methyl p-toluate and 32.8 wt.% benzene which is reacted with oxygen at 60 p.s.i.a. for 30 min. at 205° C. The liquid phase effluent is found to contain 0.69 wt.% ethylene oxide.

EXAMPLE XV

Into a pressure vessel equipped with magnetic agitation is placed a liquid charge of 3.4 wt.% ethylene and 96.6 wt.% toluene which is reacted with oxygen at 60 p.s.i.a. for 15 min. at 205° C. The liquid phase effluent is found to contain 0.83 wt.% ethylene oxide which is recoverable by distillation. Also produced is 1.21 wt.% benzaldehyde, 1.30 wt.% benzyl alcohol and benzoic acid of an undetermined amount.

EXAMPLE XVI

Into a pressure vessel equipped with magnetic agitation is placed a liquid charge of 2.9 wt.% ethylene, 56.9 wt.% m-xylene and 40.2 wt.% benzene which is reacted with oxygen at 60 p.s.i.a. for 10 min. at 205° C. The liquid phase effluent contains 1.2 wt.% ethylene oxide and a total of 5.2 wt.% of oxygenated derivatives of m-xylene. The ethylene oxide is separated by distillation as is the unreacted m-xylene. The bottoms from the m-xylene distillation, the oxygenated derivatives of m-xylene, are placed in acetic acid solvent with catalytic amounts of cobalt, manganese and bromine which reacts with the oxygen from air at 220° C and a system pressure of 300 p.s.i.g. to produce isophthalic acid.

EXAMPLE XVII

Into a pressure vessel equipped with magnetic agitation is placed a liquid charge of 3.3 wt.% ethylene, 46.8 wt.% pseudocumene and 49.1 wt.% benzene which is reacted with oxygen at 60 p.s.i.a. for 20 min. at 205° C. Ethylene oxide in an amount of 0.76 wt.% of the liquid effluent is found. About 4.7 wt.% of oxygenated pseudocumene is found which is oxidizable to trimetallic acid.

EXAMPLE XVIII

Into a pressure vessel equipped with magnetic agitation is placed a liquid charge of 3.3% ethylene, 1.99% benzyl alcohol, 2.68% benzaldehyde and 92.0% toluene which is reacted with 60 p.s.i.a. oxygen for 15 min. at 205° C. The liquid effluent is found to contain 1.47% ethylene oxide, 2.78% benzyl alcohol, 2.52% benzaldehyde and 1.53% benzoic acid. The benzy alcohol and/or the benzaldehyde could be obtained in whole or in part from a recycle stream.

EXAMPLE XIX

Into a pressure vessel equipped with magnetic agitation is placed a liquid charge of 3.4% ethylene, 6.74% benzaldehyde and 90.2% toluene which is reacted with 60 p.s.i.a. oxygen for 5 min. at 205° C. The liquid effluent is found to contain 1.28 wt.% ethylene oxide and 4.27% benzaldehyde. Benzyl alcohol and benzoic acid content was not determined. The benzaldehyde could be obtained in whole or in part from a recycle stream.

EXAMPLE XX

Into a pressure vessel equipped with magnetic agitation is placed a liquid charge of 92% p-xylene and 4.0% each of p-methyl benzyl alcohol and p-tolualdehyde which are obtainable from recycling streams and is then pressurized with oxygen to 30 p.s.i.a. and then pressurized with ethylene. The reaction mixture is heated to 175° C and reacted for 45 min. with agitation at a system pressure of 590 p.s.i.g. The liquid phase effluent is found to contain 1.15% ethylene oxide, 3.80% p-methyl benzyl alcohol, 4.20% p-tolualdehyde and 4.09% p-toluic acid.

EXAMPLE XXI

Into a pressure vessel equipped with magnetic agitation is placed a liquid charge of 92% p-xylene and 4.0% each of p-methyl benzyl alcohol and p-tolualdehyde which are obtainable from recycling streams and is then pressurized with 45 p.s.i.a. oxygen and then pressurized with ethylene. The reaction mixture is heated to 190° C and reacted for 30 min. with agitation at a system pressure of 1420 p.s.i.g. The liquid phase effluent is found to contain 1.52% ethylene oxide, 4.5% p-methyl benzyl alcohol and 4.4% p-tolualdehyde. The amount of p-toluic acid formed was not determined.

CONTINUOUS PROCESS

The process of the invention may also, of course, be carried out as a continuous rather than a batch type process as in the case of the above Examples. The simplified flow sheet shown in the accompanying drawing illustrates how this might be done.

There are three basic versions of this flow sheet. The first is as shown, with all products flowing through the oxidizer once. In this version a typical oxidation effluent is very roughly.

| 1 part | ethylene oxide |
| 3 " | ethylene |
| 2 " | p-tolualdehyde |
| 2 " | p-methyl benzyl alcohol |
| 0.25 " | p-toluic acid |
| 91.75 " | p-xylene |

This version creates a very heavy distillation load.

The second version would recycle some of the flash bottoms back to the oxidizer. This is basically a method of keeping one of the products, ethylene oxide, at a low non-reactive concentration. In this version if half of the flash bottoms are returned to the oxidizer the following distillation load would be encountered:

| 1 part | ethylene oxide |
| 3 " | ethylene |
| 1.5 " | p-tolualdehyde |
| 1.5 " | p-methyl benzyl alcohol |
| 1 " | p-toluic acid |
| 42 " | p-xylene |

The third version would differ by the performance of the oxidate column. This column would function to effect a separation between p-methyl benzy alcohol and p-toluic acid. The p-toluic acid would be the bottoms and essentially the only products with p-xylene, p-tolualdehyde and p-methyl benzyl alcohol being recycled to the oxidizer. When this version is combined with the second version with half of the flash bottoms recycling to the oxidizer the following benefits are obtained. Distillation load is moderated and ethylene oxide/oxygenated xylene fed forward ratio is improved. The following roughly typifies the distillation load and approximate compositions encountered

| 1 part | ethylene oxide |
| 3 " | ethylene |
| 3.5 " | p-tolualdehyde |
| 3.1 " | p-methyl benzyl alcohol |
| 2.9 " | p-toluic acid only material fed forward to oxidation |
| 36.5 " | p-xylene |

In some versions of the continuous process as described above some of the aromatic oxidate is recycled back to the oxidizer. These recycled oxidates are primarily the alcohols and aldehydes resulting from the oxidation in the reaction zone of the mono or poly methyl benzene. Thus it will be apparent that the process of the invention could also be carried out by separately oxidizing the mono or poly methyl benzene prior to the main oxidation reaction and then feeding the aromatic oxidate so formed into the main oxidizer, along with the ethylene and oxygen, to carry out the main reaction in the same manner as described above in connection with that modification of the continuous process wherein some aromatic oxidate is recycled. As a variation of this embodiment of the invention one could also use a derivative of a component of the oxidate, namely methyl p-toluate.

The specific examples of the invention set forth above include its use with the methyl aromatics, toluene, xylene and pseudocumene. It is contemplated that the process of the invention can also be carried out with the other methyl aromatics, specifically hemimellitene, mesitylene, prehnitene, isodurene, durene, pentamethylbenzene and hexamethylbenzene.

While the present invention has been particularly described in terms of specific embodiments thereof, it will be understood that numerous variations of the invention will be apparent to those skilled in the art. The scope of the invention is defined in each of the following claims.

I claim:

1. Process for the manufacture of ethylene oxide and an aromatic acid comprising, reacting oxygen with ethylene and a mono or poly methyl benzene in liquid phase selected from the group consisting of toluene, xylene and pseudocumene, at a temperature within the range from 150° C to 300° C and a pressure within the range from 100 p.s.i.a. to 4000 p.s.i.a. and with the ethylene in the reaction mixture within the range from 0.1 wt. % to 9 wt. %, to form an oxidate comprising the alcohol and the aldehyde of said methyl benzene and to form ethylene oxide, removing the said ethylene oxide, removing the unreacted mono or polymethyl benzene, and further oxidizing the said oxidate to the corresponding aromatic acid.

2. Process according to claim 1, in which the methyl benzene is xylene.

3. Process according to claim 1, in which the methyl benzene is p-xylene and the aromatic acid is terephthalic acid.

4. Process according to claim 1, in which the methyl benzene is m-xylene and the aromatic acid is isophthalic acid.

5. Process according to claim 1, in which the methyl benzene is toluene and the aromatic acid is benzoic acid.

6. Process according to claim 1, in which the methyl benzene is pseudocumene and the aromatic acid is trimellitic acid.

7. Process for the manufacture of ethylene oxide and an aromatic acid comprising, reacting oxygen with a mono or poly methyl benzene in liquid phase selected from the group consisting of toluene, xylene and pseudocumene to form an oxidate comprising the alcohol and the aldehyde of said methyl benzene, introducing ethylene and oxygen into said oxidate for reaction therein to form ethylene oxide, the reaction being carried out at a temperature within the range from 150° C to 300° C and at a pressure within the range from 100 p.s.i.a. to 4000 p.s.i.a. and with the ethylene in the reaction mixture within the range from 0.1 wt. % to 9 wt. %, removing the said ethylene oxide, removing the unreacted mono or polymethyl benzene, and further oxidizing said oxidate to aromatic acid.

8. Process according to claim 7, in which the methyl benzene is xylene.

9. Process according to claim 7, in which the methyl benzene is p-xylene and the aromatic acid is terephthalic acid.

10. Process according to claim 7, in which the methyl benzene is m-xylene and the aromatic acid is isophthalic acid.

11. Process according to claim 7, in which the methyl benzene is toluene and the aromatic acid is benzoic acid.

12. Process according to claim 7, in which the methyl benzene is pseudocumene and the aromatic acid is trimellitic acid.

13. Process for the manufacture of ethylene oxide comprising, reacting oxygen, ethylene, and a liquid phase oxidate formed by the reaction of oxygen with a mono or poly methyl benzene selected from the group consisting of toluene, xylene and pseudocumene, said oxidate comprising the alcohol and the aldehyde of said methyl benzene, said reaction being carried out at a temperature within the range from 150° C to 300° C, at a pressure within the range from 100 p.s.i.a. to 4000 p.s.i.a., and at a concentration of ethylene in the reaction mixture within the range from 0.1 wt. % to 9 wt. % to form ethylene oxide.

14. Process for the manufacture of ethylene oxide comprising, reacting oxygen, ethylene, and a liquid phase oxidate formed by the reaction of oxygen with a mono or polymethyl benzene selected from the group consisting of toluene, xylene and pseudocumene, said oxidate comprising the alcohol and the aldehyde of said methyl benzene, said reaction being carried out at a temperature within the range from 175° C to 250° C and at a pressure within the range from 750 p.s.i.a. to 2000 p.s.i.a., and at a concentration of ethylene in the reaction mixture within the range from 0.1 wt. % to 9 wt. % to form ethylene oxide.

15. Process according to claim 13 in which the methyl benzene is toluene.

16. Process according to claim 14 in which the methyl benzene is toluene.

17. Process according to claim 13 in which the methyl benzene is xylene.

18. Process according to claim 14 in which the methyl benzene is xylene.

19. Process according to claim 13 in which the methyl benzene is pseudocumene.

20. Process according to claim 14 in which the methyl benzene is pseudocumene.

21. Process for the manufacture of ethylene oxide and an aromatic oxidate comprising reacting oxygen with a mono or poly methyl benzene selected from the group consisting of toluene, xylene and pseudocumene to form a liquid phase oxidate comprising the alcohol and the aldehyde of said methyl benzene, reacting ethylene and oxygen in said oxidate, with the ethylene in the reaction mixture being maintained at a concentration within the range from 0.1 wt. % to 9 wt. %, the temperature of the reaction mixture being maintained within the range from 150° C to 300° C and the pressure within the range from 100 p.s.i.a. to 4000 p.s.i.a., to form ethylene oxide, removing said ethylene oxide from the reaction mixture, and removing said oxidate from the reaction mixture.

22. Process according to claim 21 in which the methyl benzene is toluene.

23. Process according to claim 21 in which the methyl benzene is xylene.

24. Process according to claim 21 in which the methyl benzene is pseudocumene.

25. Process for the manufacture of ethylene oxide which comprises reacting ethylene and oxygen in a liquid phase oxidate formed by the reaction of oxygen with a mono or poly methyl benzene and comprising the alcohol and the aldehyde of said methyl benzene, said methyl benzene being selected from the group consisting of toluene, xylene, and pseudocumene, at a temperature within the range from 150° C to 300° C, and at a pressure within the range from 100 p.s.i.a. to 4000 p.s.i.a., to form ethylene oxide and removing said ethylene oxide from the reaction mixture.

26. Process for the manufacture of ethylene oxide which comprises, feeding oxygen, ethylene and a mono or poly benzene selected from the group consisting of toluene, xylene, and pseudocumene continuously into a reaction mixture comprising the alcohol and aldehyde oxidation products of said methyl benzene, reacting the said feed materials at a temperature within the range from 150° C to 300° C and at a pressure within the range from 100 p.s.i.a. to 4000 p.s.i.a. to form ethylene oxide, withdrawing reaction mixture from the reaction zone following said reaction, removing therefrom ethylene oxide formed in the reaction, and recycling to the reaction zone some of the reaction mixture from which said ethylene oxide has been removed.

27. Process according to claim 26 in which the methyl benzene is p-xylene.

28. Process according to claim 26 in which the methyl benzene is m-xylene.

29. Process for the manufacture of ethylene oxide comprising, introducing oxygen and ethylene into an oxidate of toluene formed by the reaction of oxygen with toluene and comprising predominantly the alcohol and aldehyde oxidation products of said toluene, reacting said oxygen, ethylene, and toluene oxidate at a temperature within the range from 175° C to 250° C at a pressure within the range from 750 p.s.i.a. to 2000 p.s.i.a. and for a time within the range from 2 min. to 1 hour to form ethylene oxide, and separating from the reaction mixture ethylene oxide.

30. Process for the manufacture of ethylene oxide comprising introducing oxygen and ethylene into an oxidate of p-xylene comprising predominantly the alcohol and aldehyde oxidation products of the reaction of oxygen with p-xylene, reacting with oxygen, ethylene, and p-xylene oxidate at a temperature within the range from 175° C to 250° C at a pressure within the range from 750 p.s.i.a. to 2000 p.s.i.a. and for a time within the range from 2 min. to 1 hour to form ethylene oxide, and separating from the reaction mixture ethylene oxide.

* * * * *